US00PP35563P2

(12) United States Plant Patent
Hansen

(10) Patent No.: US PP35,563 P2
(45) Date of Patent: Dec. 26, 2023

(54) ***HOSTA* PLANT NAMED 'SOUND OF MUSIC'**

(50) Latin Name: ***Hosta* hybrid (Tratt.)**
Varietal Denomination: Sound of Music

(71) Applicant: Hans A Hansen, Zeeland, MI (US)

(72) Inventor: Hans A Hansen, Zeeland, MI (US)

(73) Assignee: Walters Gardens Inc., Zeeland, MI (US)

( * ) Notice: Subject to any disclaimer, the term of this patent is extended or adjusted under 35 U.S.C. 154(b) by 137 days.

(21) Appl. No.: 17/803,731

(22) Filed: Nov. 1, 2022

(51) Int. Cl.
*A01H 5/02* (2018.01)
*A01H 6/12* (2018.01)

(52) U.S. Cl.
USPC ..... Plt./353
CPC ..... *A01H 6/12* (2018.05)

(58) Field of Classification Search
USPC ..... Plt./353
CPC ..... A01H 5/02
See application file for complete search history.

*Primary Examiner* — Kent L Bell

(57) ABSTRACT

A new and distinct *Hosta* plant named 'Sound of Music' producing very large-sized rounded mounds of basal, broadly-cordate to rounded, giant-sized leaves with acute apices, cordate bases, slightly wavy margins and a tendency to cup downwardly toward the apex. The leaves are variegated having glaucous bluish-green margins and centers that begin the season chartreuse and become creamy-yellow as the season progresses with intermediate color separation between the margin and center of variably large segments of several shades of chartreuse. The campanulate flowers are near pale purple just above the foliage beginning in mid to late June. 'Sound of Music' is useful in the landscape, as a container plant, a specimen or en masse.

3 Drawing Sheets

Botanical classification: *Hosta* hybrid (Tratt.).
Variety denomination: 'Sound of Music'.

STATEMENT REGARDING PRIOR DISCLOSURES UNDER 37 CFR 1.77(B)(6)

*Hosta* 'Sound of Music' was first introduced by the inventor as a non-enabling description in registration of the name in early 2021 with the International Cultivar Registration Authority for the genus *Hosta*. No plants of *Hosta* 'Sound of Music' have been sold in this country or anywhere in the world, nor has any enabling disclosure of the new plant been made.

BACKGROUND AND ORIGIN OF THE PLANT

The present invention relates to a new and distinct *Hosta* plant, *Hosta* 'Sound of Music' hereinafter also referred to as the new plant or by the cultivar name 'Sound of Music'. *Hosta* 'Sound of Music' was hybridized by the inventor on Jun. 14, 2012, at a wholesale perennial nursery in Zeeland, Michigan, USA. The female parent was the proprietary unreleased seedling known only by the code WGI-07 (not patented) and the male parent was 'Empress Wu' U.S. Plant Pat. No. 20,774. The seeds from this cross were collected and planted in the fall of 2012 and a single seedling from this cross eventually was selected as the new plant. The new plant was assigned the breeder code 12-50-2 and passed the initial evaluation in the summer of 2016. 'Sound of Music' has been asexually propagated by division at the same nursery since 2018 and also by careful shoot tip plant tissue culture with the resultant asexually propagated plants having retained all the same traits as the original plant. *Hosta*

'Sound of Music' has been stable and reproduced true to type plants in successive generations of asexual reproduction.

There are over 7,000 registered and established *Hosta* cultivars with The American *Hosta* Society, which is the International Cultivar Registration Authority for the genus *Hosta*. Several of these have blue-green leaf blades. The most similar *Hosta* cultivars known to the applicant are: 'Alligator Alley' (not patented), 'Andrew' (not patented), 'Dream Weaver' (not patented), 'Hudson Bay' U.S. Plant Pat. No. 23,598, 'Lakeside Beach Captain' (not patented), 'Lakeside Shoremaster' U.S. Plant Pat. No. 32,068, and 'When I Dream' U.S. Plant Pat. No. 34,285.

The female parent is smaller in habit with smaller, more bullate, more upwardly facing cupped, more glaucous foliage that is randomly streaked with creamy yellow variegation, and the scapes are shorter. 'Empress Wu' has a larger habit, more broadly ovate foliage that is solid deep green, the scapes are taller and more horizontal habit with more glaucous, solid bluish-green colored foliage.

'Alligator Alley' has a smaller habit, with smaller and more ovate foliage. 'Andrew' has a smaller habit with smaller foliage and the center is more white. 'Dream Weaver' has a smaller habit with smaller foliage and the flowers are more white. 'Hudson Bay' has a slightly smaller leaf and smaller habit, and the leaf center is proportionally smaller. 'Lakeside Beach Captain' has a smaller habit, smaller leaves, and the margin is wider in proportion and the center is narrower. 'Lakeside Shoremaster' is smaller in habit and has smaller foliage that is less rounded and more ovate. 'When I Dream' is longer, less rounded foliage with more acute apex, the margin is more sinuate the habit is smaller, and the flowers are lighter pale lavender on shorter scapes.

Other *Hosta* cultivars may have individual traits similar to 'Sound of Music', but the new plant differs from the above-listed cultivars and all other *Hostas* known to the applicant by the combination of the following traits:

1. Leaves are giant-sized, broadly-cordate to rounded, with acute apices and cordate bases;
2. Leaves have a slightly wavy margin, moderately bullate surface between the veins, and deeply impressed adaxial veins, with a tendency for the leaf ends to cup downward;
3. Leaf margins are moderately glaucous bluish-green, and the center color emerges chartreuse becoming creamy yellow as the season progresses;
4. Leaves have a series of intermediate colors of several shades of chartreuse between the margin and center of variably large segments;
5. Campanulate flowers are pale purple on upright scapes beginning in mid to late June;
6. Flowers are subtended by a lightly blushed bract of similar hue to flowers and densely arranged on scapes with the first flowers beginning to open just above the foliage;
7. The habit is a very large-sized rounded mound.

BRIEF DESCRIPTION OF THE DRAWINGS

The photographs of the new plant demonstrate the overall appearance of the new plant, including the unique traits. The colors are as accurate as reasonably possible with color reproductions. Ambient light spectrum, temperature, source and direction may cause the appearance of minor variation in color.

The drawings show a plant of 'Sound of Music' in a trial garden at a nursery in Zeeland, MI with supplement fertilizer and water as needed.

DETAILED BOTANICAL DESCRIPTION

Figure 1:
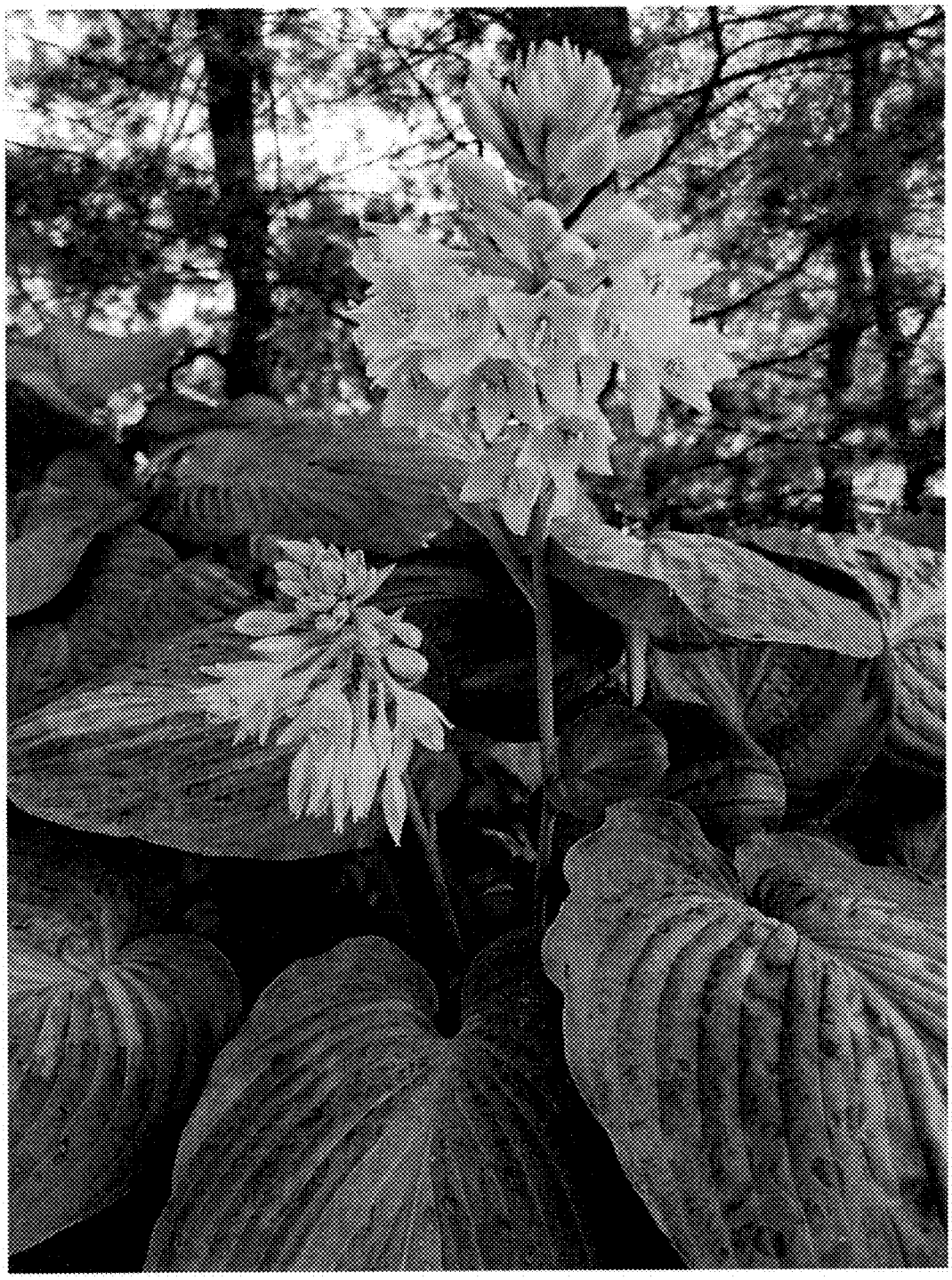
FIG. 1 shows the landscape habit of a nine-year-old plant.
Figure 2:
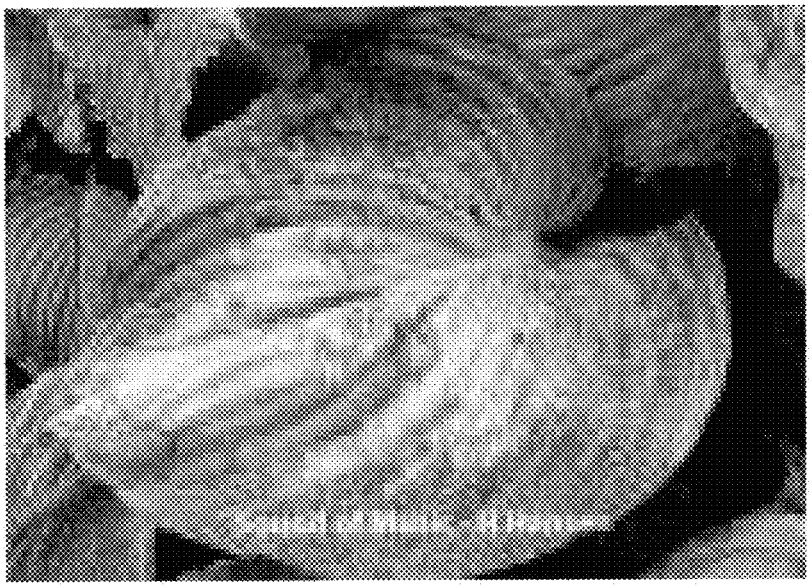
FIG. 2 shows a close-up of a leaf from a nine-year-old plant prior to flowering.
Figure 3:
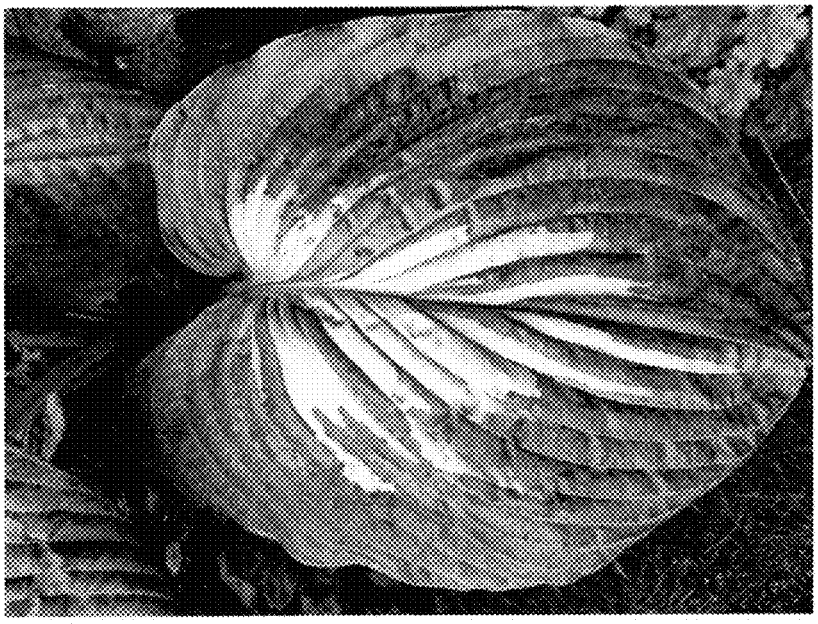
FIG. 3 shows a close-up of a leaf from a nine-year-old plant after flowering.
Figure 4:
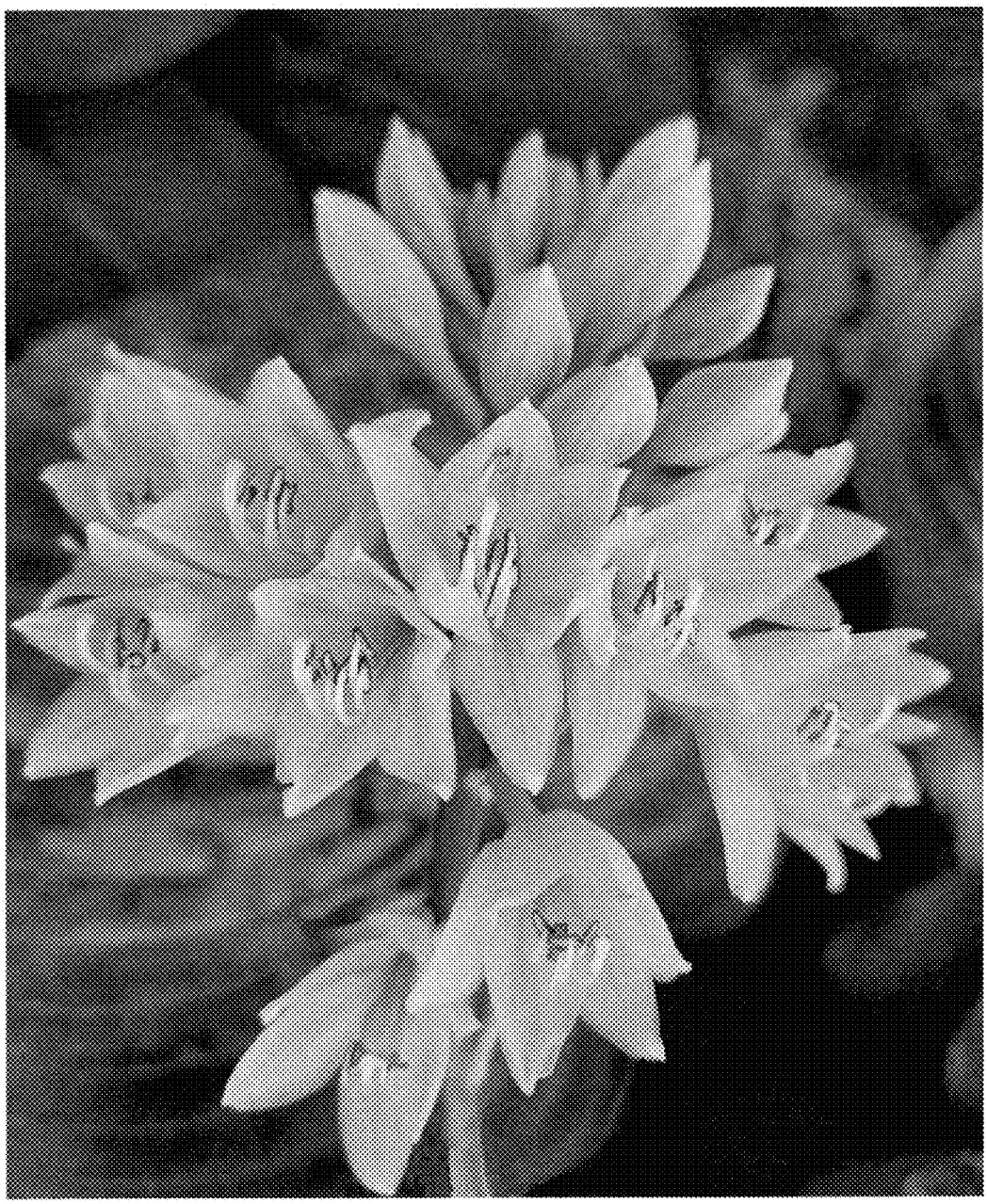
FIG. 4 shows a close-up of the flowers, buds, and foliar bracts of a nine-year-old plant.

The following descriptions and color references are based on the 2015 edition of The Royal Horticultural Society Colour Chart except where common dictionary terms are used. The new plant, *Hosta* 'Sound of Music', has not been observed under all possible environments. Those skilled in the art will appreciate that certain characteristics will vary with plants that are more mature or plants that are less mature. The phenotype may vary slightly with different environmental conditions, such as temperature, light, fertility, moisture and maturity levels, but without any change in the genotype. The following observations and size descriptions are of a five-year-old plant in a shaded trial garden in Zeeland, Michigan with supplemental water and fertilizer.

Botanical classification: *Hosta* x hybrid;

Parentage: Female or seed parent is a proprietary hybrid known only as WGI-07; male or pollen parent is 'Empress Wu';

Propagation: Garden division and sterile shoot tip tissue culture;

Time to initiate roots from tissue culture: About three to four weeks;

Growth rate: Moderately vigorous to slow;

Crop time: About four months to six months to finish during the spring in a one-liter container from rooted tissue culture plantlet during the warm portion of the growing season;

Rooting habit: Fleshy, lightly branching;

Root color: Nearest RHS NN155C when actively growing;

Plant shape and habit: Hardy herbaceous perennial with basal rosette of leaves emerging from rhizomes producing a very large-sized mound of outwardly arching petioles and leaves and mostly erect scapes flowering just above the foliage;

Plant size: Foliage height to about 76 cm above soil line to the top of the leaves, to about 95 cm tall to the top of the flowers and to about 160 cm wide at the widest point about 20 cm above the soil line;

Foliage description: Broadly-cordate to rounded; acute apex; cordate base with lobes nearly overlapping; margin entire, and weakly sinuate; not folded, with distal portion frequently curved downward producing an inverted cupped form; surface moderately bullate between the veins; glabrous and moderately glaucous both surfaces; flexible; variegated;

Leaf blade size: To about 42 cm long and about 35.5 cm wide about halfway from the petiole; average about 38 cm long and 33.5 cm wide;

Leaf blade color: Early season and expanding adaxial margin nearest RHS 138A, center nearest RHS 146D with intermediate zone comprising nearest RHS 146C, abaxial margin between RHS N138B and RHS 138A, center RHS 146C with intermediate zone comprising nearest RHS N139D and between RHS 146C and RHS N138B; mid-season and mature adaxial margin between RHS 139A and RHS 189B, center nearest RHS 8D, with intermediate zone comprising colors of between RHS 144A and RHS N144C, between RHS 139D and RHS N138D, between RHS N138D and RHS 189B, abaxial margin between RHS 189C and RHS 138C, center nearest RHS 150D, with intermediate zone comprising colors of between RHS 138C and RHS 138D, nearest RHS 147D, and between RHS 148D and RHS 144C;

Veins: 15 to 17 pairs with midrib; deeply impressed adaxial and costate and smooth abaxial;

Vein color: Adaxial distal margin region nearest RHS N138C and proximally nearest RHS 194A, abaxial midrib nearest RHS 193D, primary veins near midrib nearest RHS 193B, primary veins in distal margin region between RHS N138C and RHS 191B; emerging adaxial veins nearest RHS 145A, abaxial midrib nearest RHS 145D and primary veins nearest RHS 146D;

Petiole: Glabrous and matte both adaxial and abaxial; deeply concavo-convex; stiff; to 51.5 cm long and 35 mm wide at base and about 16 mm deep at base, average about 46 cm long and 30 mm wide and 13 mm deep;

Petiole color: Adaxial margin between RHS 189B and RHS N138A, center between RHS 138C and RHS 145B, abaxial margin between RHS 189B and RHS N138A, midrib nearest RHS 145D, and region surrounding midrib nearest RHS 146C;

Flower description:

Buds one to two days prior to opening: Clavate with acute apex and narrow tube and rounded base; about 45 mm long and 11 mm in diameter at the widest portion in the bulb, tube to about 19 mm long and to about 3 mm diameter at base, tapering below bulb;

Bud color: Bulb portion between RHS 85C and RHS 85D, tube portion between RHS 85D and RHS 85C, base of bulb portion distal to tube nearest RHS NN155D;

Flowers: Perfect; incomplete; campanulate flaring distally; attitude slightly downwardly; to 53 mm long to exserted pistil; corolla to 50 mm long and 28 mm wide at apex, corolla tube portion 22 mm long and gradually tapering to 3 mm diameter at base, decreasing in size distally; with rounded base; flowers tightly arranged on scape; aspect mostly horizontal;

Flowering lasting: Persists for a normal period, usually about one day on plant;

Flowering period: Scapes remain effective with flowers beginning mid to late June for about three to three and a half weeks; with about 55 flowers per scape; mostly secund;

Fragrance: No detectable fragrance;

Tepal: Two sets of three, nearly identical; elevate; entire margins; acute apex; fused in basal 30 mm; glabrous adaxial and abaxial; outer set to about 11 mm wide and 50 mm long; inner set to about 50 mm long and 12 mm wide, with 1 mm wide translucent margin;

Tepal color: Outer set adaxial center between RHS 85C and RHS 85D with distal veins nearest RHS 85C, without translucent margin and outer edge of flared portion NN155D; tube portion nearest RHS NN155D; abaxial flared portion between RHS 85D and RHS NN155D, tube portion nearest RHS 85D with basal 2 mm nearest RHS 85C; inner set adaxial distal portion between RHS 85C and RHS 85D with distal veins nearest RHS 85C and 1 mm translucent margin and edge of flared portion nearest RHS NN155D; tube portion nearest RHS NN155D; abaxial flared portion between RHS 85D and RHS NN155D, tube portion nearest RHS 85D with basal 2 mm nearest RHS 85C;

Gynoecium: Single; to, about 58 mm long; superior;

*Style*.—Cylindrical; glabrous; to about 51 mm long and 0.7 mm diameter; straight with distal 5 mm arcuate upwards about 90°; color nearest RHS 155C.

*Stigma*.—Puberulent; globose; about 1 mm long and 1.5 mm diameter; color between RHS 155C and RHS 155B.

*Ovary*.—Oblong ellipsoidal; superior; apex rounded; base rounded to truncate; sides nearly smooth; about 7 mm long and 3 mm diameter; color nearest RHS 146C.

Androecium: Six;

*Filaments*.—Six; cylindrical; approximately 54 mm long and 0.5 mm in diameter; curved upwardly about 90° in the distal 5 mm; color in distal one-half nearest RHS 157D transitioning to nearest RHS I45C proximally.

*Anthers*.—Oblong with rounded ends; dorsifixed, longitudinally dehiscent; about 5 mm long and 2 mm wide when fully developed; color adaxial nearest RHS 177D, abaxial nearest RHS 195B.

*Pollen*.—Abundant; spherical; less than 0.1 mm long; color nearest RHS 17.;

Peduncle: Cylindrical; usually one per mature division; about 4 per plant; glabrous; moderately glaucous; erect to arching with maturity; to about 95 cm tall, and about 13 mm in diameter at base, average about 78 cm tall and 8 mm diameter at base;

Inflorescence: Flowering portion about 24 cm long and 7 cm wide; with single bract subtending each flower;

Peduncle color: Variable, when flowering nearest RHS N138C; after flowering season proximally between RHS 145A and RHS 192B, distally nearest RHS 196D;

Pedicel: Cylindrical; glabrous; slightly lustrous; curved slightly downward; to about 18 mm long and 2 mm diameter, decreasing distally;

Pedicel color: Between RHS 145A and RHS 145B;

Floral bracts: Each flower normally subtended by a single bract; lanceolate; narrowly acute apex and truncate clasping base; entire margin; strongly concavo-convex; glabrous and slightly glaucous abaxial and adaxial; to about 52 mm long 14 mm wide, decreasing distally;

Bract color: Proximal bracts at time or flowering adaxial longitudinal center between RHS 145D and RHS 160D, margins nearest RHS 146A; and proximal bract abaxial longitudinal center between RHS 145D and RHS 160D; distal bracts adaxial and abaxial surfaces nearest RHS 84D with a moderate overtone of nearest RHS 145B distally;

Fruit: Non-fleshy, dehiscent, tri-loculicidal capsule; oblong; rounded base; acute to apiculate apex; about 36 mm long and 8 mm in diameter; color as maturing between RHS 145D and RHS 146D, upon dehiscence nearest RHS 161C;

Seeds: Elliptic; with flattened wing surrounding embryo positioned toward one end of ellipse; to about 13 mm long, 3 mm wide and 1 mm thick at embryo; typically 24 to 42 per capsule; color between RHS 200A and RHS 202A with maturity;

Disease and pest resistance: The thick glaucous leaves provide some resistance to slug feeding. Other resistance to pests (including: *Odocoilcus virginianus* and *Oryctotagus cuniculus*) and diseases common to *Hostas* is equal that typical of other cultivars.

Growth: The plant grows best and shows best coloration with plenty of moisture, adequate drainage and light shade, but the plant is able to tolerate some drought when mature.

Hardiness: At least from USDA zone 3 through 8.

It is claimed:

1. A new and distinct *Hosta* plant named 'Sound of Music' as herein described and illustrated.

* * * * *